US00PP32888P2

(12) United States Plant Patent
Koot

(10) Patent No.: US PP32,888 P2
(45) Date of Patent: Mar. 9, 2021

(54) ***PETUNIA* PLANT NAMED 'DOPETSWEEWHI'**

(50) Latin Name: ***Petunia* X *hybrida***
Varietal Denomination: Dopetsweewhi

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/873,880

(22) Filed: Aug. 4, 2020

(51) Int. Cl.
*A01H 6/82* (2018.01)
*A01H 5/02* (2018.01)

(52) U.S. Cl.
USPC ..... Plt./356.21

(58) Field of Classification Search
USPC ..... Plt./356.21
See application file for complete search history.

(56) References Cited

PUBLICATIONS

PLUTO Plant Variety Database Sep. 19, 2020. p. 1.*

* cited by examiner

*Primary Examiner* — Annette H Para
(74) *Attorney, Agent, or Firm* — C. Anne Whealy

(57) ABSTRACT

A new and distinct cultivar of *Petunia* plant named 'Dopetsweewhi', characterized by its upright and mounding plant habit; moderately vigorous growth habit; freely branching habit; early and freely flowering habit; large white-colored flowers; and good garden performance.

1 Drawing Sheet

Botanical designation: *Petunia* X *hybrida*.
Cultivar denomination: 'DOPETSWEEWHI'.

CROSS-REFERENCED TO A RELATED APPLICATION AND STATEMENT REGARDING PRIOR DISCLOSURES BY INVENTOR AND APPLICANT

This application claims priority to a European Community Plant Breeders' Rights application filed on Nov. 14, 2019, application number 2019/2982. There have been no offers for sale anywhere in the world prior to the effective filing date of this Application and no accessibility to one of ordinary skill in the art could have been derived from the printed Plant Breeder's Rights documents.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Petunia* plant, botanically known as *Petunia* X *hybrida* and hereinafter referred to by the name 'Dopetsweewhi'.

The new *Petunia* plant is a product of a planned breeding program conducted by the Inventor in Rheinberg, Germany. The objective of the breeding program is to create new freely branching and early-flowering *Petunia* plants with numerous attractive flowers.

The new *Petunia* plant originated from a cross-pollination made by the Inventor in July, 2016 in Rheinberg, Germany of a proprietary selection of *Petunia* X *hybrida* identified as code number TT-0632, not patented, as the female, or seed, parent with a proprietary selection of *Petunia* X *hybrida* identified as code number TT14-007865-001, not patented, as the male, or pollen, parent. The new *Petunia* plant was discovered and selected by the Inventor as a single flowering plant from within the progeny of the stated cross-pollination in a controlled greenhouse environment in Rheinberg, Germany in May, 2019.

Asexual reproduction of the new *Petunia* plant by terminal vegetative cuttings in a controlled greenhouse environment in Rheinberg, Germany since June, 2019 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dopetsweewhi'. These characteristics in combination distinguish 'Dopetsweewhi' as a new and distinct *Petunia* plant:

1. Upright and mounding plant habit.
2. Moderately vigorous growth habit.
3. Freely branching habit.
4. Early and freely flowering habit.
5. Large white colored flowers.
6. Good garden performance.

Plants of the new *Petunia* can be compared to plants of the female parent selection. In side-by-side comparisons, plants of the new *Petunia* differ primarily from plants of the female parent selection in flower shape as plants of the new *Petunia* have more rounded, that is, less star-shaped, flowers than plants of the female parent selection.

Plants of the new *Petunia* can be compared to plants of the male parent selection. In side-by-side comparisons, plants of the new *Petunia* differ primarily from plants of the male parent selection in growth habit as plants of the new *Petunia* are more vigorous than and not as compact as plants of the male parent selection.

Plants of the new *Petunia* can be compared to plants of *Petunia* X *hybrida* 'Kesupite', not patented. In side-by-side comparisons, plants of the new *Petunia* and 'Kesupite' differ primarily in the following characteristics:

1. Plants of the new *Petunia* are more compact than and not as vigorous as plants of 'Kesupite'.
2. Plants of the new *Petunia* have smaller leaves than plants of 'Kesupite'.
3. Plants of the new *Petunia* are more freely flowering than plants of 'Kesupite'.

BRIEF DESCRIPTION OF THE PHOTOGRAPH

The accompanying colored photograph illustrates the overall appearance of the new *Petunia* plant showing the colors as true as it is reasonably possible to obtain in colored reproductions of this type. Colors in the photograph may differ slightly from the color values cited in the detailed botanical description which accurately describe the colors of the new *Petunia* plant.

The photograph is a side perspective view of a typical flowering plant of 'Dopetsweewhi' grown in a container.

DETAILED BOTANICAL DESCRIPTION

The aforementioned photograph and following observations, measurements and values describe plants grown during the spring in 22-cm containers in a glass-covered greenhouse in Rheinberg, Germany and under cultural practices typical of commercial *Petunia* production. During the production of the plants, day and night temperatures averaged 18° C. and light levels averaged 4,500 lux. Plants were twelve weeks old when the photograph and description were taken. In the following description, color references are made to The Royal Horticultural Society Colour Chart, Fifth Edition, 2007, except where general terms of ordinary dictionary significance are used.

Botanical classification: *Petunia* X *hybrida* 'Dopetsweewhi'.

Parentage:

*Female, or seed, parent*.—Proprietary selection of *Petunia* X *hybrida* identified as code number TT-0632, not patented.

*Male, or pollen, parent*.—Proprietary selection of *Petunia* X *hybrida* identified as code number TT14-007865-001, not patented.

Propagation:

*Type*.—By terminal vegetative cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; close to 155B in color, actual color of the roots is dependent on substrate composition, water quality, fertilizers, substrate temperature and age of roots.

*Rooting habit*.—Freely branching; dense.

Plant description:

*Plant and growth habit*.—Upright and mounding to spreading plant habit; freely branching habit with about ten to twelve primary lateral branches each with about eight secondary branches developing after pinching; moderately vigorous growth habit; moderate growth rate.

*Plant height, soil level to top of foliar plane*.—About 20 cm.

*Plant height, soil level to top of floral plane*.—About 20 cm.

*Plant diameter*.—About 40 cm.

Lateral branch description:

*Length*.—About 30 cm.

*Diameter*.—About 5 mm.

*Internode length*.—About 3 cm.

*Strength*.—Moderately strong.

*Aspect*.—Initially upright to outwardly spreading.

*Texture and luster*.—Pubescent; semi-glossy.

*Color, developing*.—Close to 146A.

*Color, developed*.—Close to 146B.

Leaf description:

*Arrangement*.—Before flowering, alternate; after flowering, opposite; simple.

*Length*.—About 3.3 cm.

*Width*.—About 1.7 cm.

*Shape*.—Spatulate.

*Apex*.—Obtuse.

*Base*.—Attenuate.

*Margin*.—Entire.

*Texture and luster, upper and lower surfaces*.—Pubescent; leathery; semi-glossy.

*Venation pattern*.—Pinnate; arcuate.

*Color*.—Developing leaves, upper surface: Close to 135B. Developing leaves, lower surface: Close to 137C. Fully expanded leaves, upper and lower surfaces: Close to 137B; venation, close to 137C.

*Petioles*.—Length: About 1.2 mm. Diameter: About 2 mm. Strength: Moderately strong; firm. Texture and luster, upper and lower surfaces: Smooth, glabrous; matte. Color, upper and lower surfaces: Close to 139C.

Flower description:

*Flower type and flowering habit*.—Single salverform flowers arising from leaf axils; freely flowering habit with usually about 350 flowers and flower buds developing per plant; flowers face mostly upright to outwardly.

*Fragrance*.—None detected.

*Natural flowering season*.—Plants flower continuously during the spring and summer in Germany; early flowering habit, plants typically beginning flowering about nine weeks after planting.

*Flower longevity*.—Individual flowers last about two to three days on the plant; flowers persistent.

*Flower buds*.—Length: About 3 cm. Diameter: About 4.9 mm. Shape: Ovoid. Texture and luster: Rippled; semi-glossy. Color: Close to 144C.

*Flower diameter*.—About 5.7 cm.

*Flower depth* (*height*).—About 5.6 cm.

*Flower throat diameter*.—About 8.4 mm.

*Flower tube length*.—About 2.7 cm.

*Flower tube diameter*.—About 2.2 mm.

*Corolla*.—Arrangement: Five petals fused at the base and opening into a flared trumpet. Petal lobe length (from throat): About 2.4 cm. Petal lobe width: About 2.4 cm. Petal shape: Roughly spatulate. Petal apex: Obtuse. Petal margin: Entire; slightly undulate. Petal texture and luster, upper and lower surfaces: Rippled, glabrous; semi-glossy. Throat texture and luster: Rippled, glabrous; semi-glossy. Tube texture and luster: Rippled, pubescent; semi-glossy. Color: Petal lobe, when opening, upper surface: Close to 155D. Petal lobe, when opening, lower surface: Close to 150D. Petal lobe, fully opened, upper and lower surfaces: Close to 155D; venation, close to 145A; color does not change with development. Flower throat: Close to 155D and 150B; venation, close to 145A. Flower tube: Close to 155D; venation, close to 145A.

*Sepals*.—Arrangement: Five sepals fused at the base forming a tubular star-shaped calyx. Length: About 1.3 cm. Diameter: About 2.7 mm. Shape: Oblong. Apex: Rounded. Base: Decurrent. Margin: Entire. Texture and luster, upper and lower surfaces: Smooth, glabrous; semi-glossy. Color: When opening, upper surface: Close to 137B. When opening, lower surface: Close to 137C. Fully opened, upper surface: Close to 137A. Fully opened, lower surface: Close to 137B.

*Peduncles*.—Length: About 2.1 cm. Diameter: About 2 mm. Strength: Moderately strong. Texture and luster: Smooth, glabrous; semi-glossy. Color: Close to 144A.

*Reproductive organs*.—Stamens: Quantity per flower: Five. Filament length: About 2.3 cm. Filament color: Close to 155D. Anther length: About 2 mm. Anther shape: Ovate. Anther color: Close to 155A. Pollen amount: Abundant. Pollen color: Close to 158A. Pistils: Quantity per flower: One. Pistil length: About 2.2 cm. Style length: About 2.1 cm. Style color: Close to 145D. Stigma diameter: About 1.5 mm. Stigma shape: Rounded. Stigma color: Close to 145A. Ovary color: Close to 146C. Fruits: Quantity produced per plant: About 280 during the flowering season. Length: About 6 mm. Diameter: About 4.5 mm. Texture: Smooth, glabrous. Color: Close to 165D. Seeds: Quantity per flower: About 90. Length: About 0.3 mm. Diameter: About 0.3 mm. Texture: Smooth, glabrous. Color: Close to 200A.

Garden performance: Plants of the new *Petunia* have been observed to have good garden performance and tolerate wind, rain, temperatures ranging from about 5° C. to about 40° C. and to be suitable for USDA Hardiness Zone 11.

Pathogen & pest resistance: To date, plants of the new *Petunia* have not been observed to be resistant to pathogens and pests common to *Petunia* plants.

It is claimed:

1. A new and distinct *Petunia* plant named 'Dopetsweewhi' as illustrated and described.

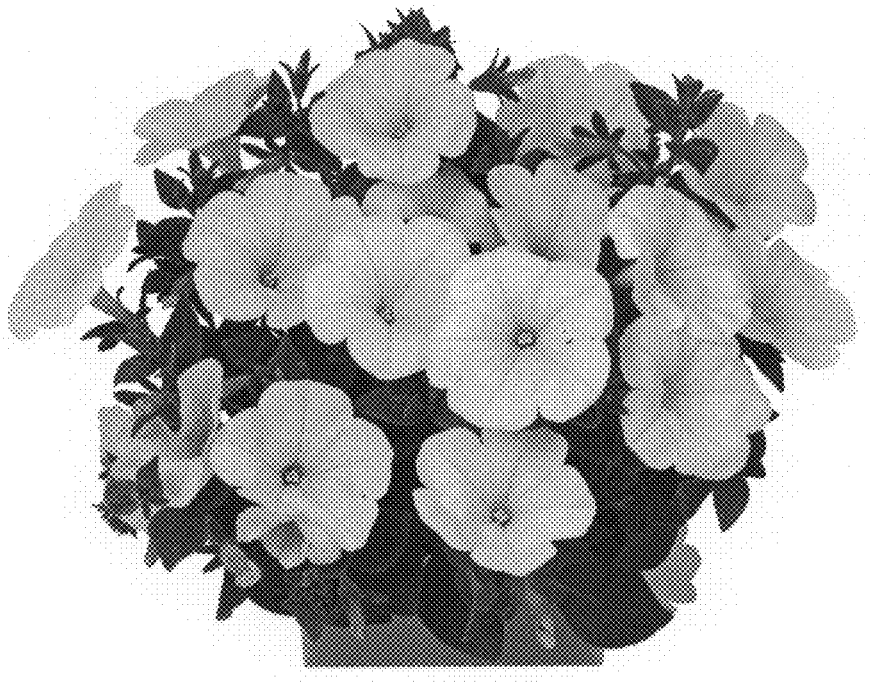

* * * * *